(12) United States Patent
Wunder

(10) Patent No.: US 7,858,394 B2
(45) Date of Patent: Dec. 28, 2010

(54) TEST METHODS FOR DETERMINING THE INTRACELLULAR CONCENTRATION OF CYCLIC NUCLEOTIDES

(75) Inventor: Frank Wunder, Wuppertal (DE)

(73) Assignee: Axxam SpA, Milan (IT)

( * ) Notice: Subject to any disclaimer, the term of this patent is extended or adjusted under 35 U.S.C. 154(b) by 0 days.

(21) Appl. No.: 10/549,014

(22) PCT Filed: Mar. 6, 2004

(86) PCT No.: PCT/EP2004/002317

§ 371 (c)(1),
(2), (4) Date: Jun. 22, 2006

(87) PCT Pub. No.: WO2004/083803

PCT Pub. Date: Sep. 30, 2004

(65) Prior Publication Data

US 2007/0031834 A1 Feb. 8, 2007

(30) Foreign Application Priority Data

Mar. 18, 2003 (DE) .............................. 103 11 769

(51) Int. Cl.
*G01N 33/566* (2006.01)
(52) U.S. Cl. .................. 436/501; 435/7.1; 435/7.2; 435/7.21; 435/8; 435/363
(58) Field of Classification Search .................. None
See application file for complete search history.

(56) References Cited

U.S. PATENT DOCUMENTS 7,052,857 B2 * 5/2006 Zoller et al. ............... 435/7.21

7,115,377 B2 * 10/2006 Yao et al. ..................... 435/7.1

FOREIGN PATENT DOCUMENTS

DE 101 38 876 A1 3/2003

OTHER PUBLICATIONS

Altenhofen et al., Control of ligand specificity in cyclic nucleotide-gated channels from rod photoreceptors and olfactory epithelium, Nov. 1991, P.N.A.S. 88:9868-9872.*
Maeda et al., Generation of cell transfectants expressing cardiac calcium ion channel and calcium indicator protein aequorin, 1996, Anal. Biochem. 242:31-39.*
Renard et al., Development of an inducible NMDA receptor stable cell line with an intracellular Ca2+ reporter, 1999, Euro. J. Pharm. 366:319-328.*
Ungrin et al., An automated aequorin luminescence-based functional calcium assay for G-protein-coupled receptors, 1999, Anal. Biochem. 272:34-42.*
Sautter, A., et al., "An isoform of the rod photoreceptor cyclic nucleotide-gated channel beta subunit expressed in olfactory neurons", Proc. Natl. Acad. Sci. USA, 95: 4696-4701 (Apr. 1998).

* cited by examiner

*Primary Examiner*—John D Ulm
(74) *Attorney, Agent, or Firm*—Edwards Angell Palmer & Dodge LLP; Ralph A. Loren; Amy DeCloux

(57) ABSTRACT

The invention relates to methods for the quantitative optical analysis of the intracellular concentration of the cyclic nucleotides cGMP and cAMP, said methods using cell lines which express a combination of certain CNG channels, a calcium-sensitive photoprotein, and different target proteins for which modulators are to be found, in a recombinant manner. The cell lines modified in this way are suitable for high-throughput screening (HTS and uHTS) and can be used to identify medicaments which influence the activity of receptors or enzymes participating in the composition or decomposition of the cyclic nucleotides cGMP and cAMP.

20 Claims, 5 Drawing Sheets

SEQUENCE LISTING

<160> NUMBER OF SEQ ID NOS: 5

<210> SEQ ID NO 1
<211> LENGTH: 3166
<212> TYPE: DNA
<213> ORGANISM: Bos taurus

<400> SEQUENCE: 1

```
gctcacctac tggcaggctg gggtgtgcag gccccacagt gagagggtca gacatccagc    60
cagtgggcag aactgtttct ccagtgggca agtgctgccc tgggccgagg cctcgacctc   120
gcctcagctg taggcatggg ctcctctgag tcactgccgg cctcccctgc tggcctcagg   180
cagggcgggc agctctttga ctgagaggct gagaagctgc gtggggattc ggggatcccc   240
ctggtctggg gacaggagct ttgggaggtc tctactgtcc cttggtgctg atgagctccc   300
gagggttcgt ctctgactgg aagcttcttg gacagaccta tagcctgtgg ccaagggaca   360
ccctgcctcg gaatccgtct ggtgaggaaa ggtgagggtc ctggttgtac atggaggatg   420
acagaaaaag ccaatggcgt gaagagctcc ccagccaata accacaacca ccatgcccct   480
cctgccatca aggccagtgg caaagatgac cacagggcca gcagccggcc acagtctgct   540
gctgctgatg acacctcctc agagctacag caactggcag agatggatgc cccccagcag   600
aggaggggtg gcttccgcag gattgcccgc ctggtggggg tcctcagaga gtgggcttac   660
aggaacttcc gtgaggagga gcctagacct gactcattcc ttgagcgttt ccggggggct   720
```

-continued

```
gagctccaca ccgtgacaac acaacaagga gacggcaaag gcgacaagga cggcgagggc      780
aagggcacca agaagaagtt tgaactcttt gtcttggacc cagccgggga ctggtactac      840
cgctggcttt ttctcattgc cttgcccgtc ctctacaact ggtgcctatt ggtggccaga      900
gcctgcttca gtgacctgca gaaaggctac tacatagtgt ggctggtgct ggattacgtc      960
tcagatgtgg tctacatcgc agacctcttc atccgactgc gcacaggttt cttggagcag     1020
gggctactgg tgaaagacac caagaagttg cgggacaact acatccacac catgcagttt     1080
aagctggatg tggcctccat catccctaca gacctgatct attttgctgt ggggatccat     1140
aaccctgagg tgcgcttcaa ccgcctgcta cactttgccc gcatgtttga gttctttgac     1200
cgcactgaga cacgcaccag ctaccccaac atcttccgaa taagcaacct gatcctctac     1260
atcttgatca tcattcactg gaatgcctgc atctactatg ccatctccaa gtccatcggc     1320
tttggggtag acacctgggt ttaccccaac atcactgacc ctgagtatgg ctacctgtct     1380
agggagtaca tctattgcct ttactggtct acactgaccc tcaccaccat ggggagaca      1440 ccaccccctg taaaggatga ggagtacctg tttgtcatct ttgacttcct gattggtgtc     1500
ctcatctttg ccaccatcgt gggaaatgtg ggctccatga tctccaacat gaatgccacc     1560
cgggctgagt tccaggccaa gattgatgct gtcaaacatt atatgcagtt ccgaaaggtc     1620
agcaaggaga tggaagccaa ggtcattagg tggtttgact acttgtggac caataagaag     1680
agtgtagatg agcgagaagt cctcaaaaac ctgccagcaa agctcagggc tgagatagcc     1740
atcaacgtcc acctgtccac actcaagaaa gtgcgcatct ttcaggactg tgaggctggc     1800
ctgctggtgg aactggtatt aaagctccgg cctcaggtct ttagccctgg ggactacatt     1860
tgccgcaagg gggatattgg gaaggagatg tacataatca aggagggaaa attggcagtg     1920
gtggctgatg acggtgtcac tcagtatgcc ctgctctcgg ctgggagttg ctttggagag     1980
atcagtatcc ttaatattaa gggcagcaaa atgggcaatc ggcgcacagc caacatccgc     2040
agtcttggct actctgatct gttctgcttg tccaaggatg atcttatgga agctgtgact     2100
gagtaccctg atgccaagag ggtcttggag gagagaggcc gggagattct gatgaaggag     2160
ggcttgttgg atgagaatga ggtggcagcc agcatggagg tagatgtgca ggaaaagcta     2220
gaacagctgg agaccaacat ggacaccttg tacactcgtt ttgcccgcct gctggccgag     2280
tacacgggag cccagcagaa gctcaagcag cgcatcacag ttttggaaac gaagatgaag     2340
cagaataatg aggatgactc cctgtcagat gggatgaaca gcccagagcc acctgccgag     2400
aagccataat ggcttggccc aattgcccct ccagccttgg ctttgacccc agggctggaa     2460
gagctgtgta ggtccccaca tatatatgca ttaccacatc cccttgaatt ctcccagaag     2520
cctctctgct ggaaggttta gggctcgatc atccagaagc cctcctccaa gtccgactaa     2580
cagctaatct tgtgcagggc atagactgtg cttagctcgg cttccagaag cttcagcctg     2640
tctaagtttg aggaagaaag aaaagaggag catctctcca ggctcttttg catctagtta     2700
cctcctactt gattctttc taatatgtgt tctgaatatt ccatttccc tgcagcagta      2760 tgtagttaga acactggctg cagacaccca gcactggtcc cagtgtcctt ttcccaaggc     2820
aggcaaaagg tgtggagggg ggcaaggagg agatgctcac tccaagtcct gccgtgctga     2880
ttcctccgcc tgtctgccaa cccagagtgg gagccctgtg gtcttttctg aaccaggggg     2940
aggaggatgc tcctggtctc aatccatcc caggacatgg agtgaggaac tagcagttgg      3000
ccagcaggca aggcacctgg agaaggtggt gggcaggagc ctggccatca cccctctatg     3060
cagagtgttt ctcaggaggc cctgaggctg atggtgggtg gatgactctt caagttaaca     3120
```
tctgcagtag agacacttac aagttaataa attcctctga actttt         3166

<210> SEQ ID NO 2
<211> LENGTH: 3236
<212> TYPE: DNA
<213> ORGANISM: Rattus norvegicus

<400> SEQUENCE: 2
caccagctcc atgctgtgcc aatcacagcg tcttagaagc tgctgtcctg gctgacccag         60
ggcttctccc ggctccactc atatgctcca gtcccaggct tggcatcact gtcacagccc        120
caggctgacc tactgcaaca tggaccttcc taccagcaga gcccgaaaga cccaatgtcc        180
tgctggatag ctgtttggtg gtgcaggctg atgtggacca gtgccagcta gaaagggcac        240
agccagagac agcatcgatc caggagttac agaagaaga agaggagaag gaggaagaga        300
agaaggagga ggaagaggag aaggaggagg aggaagagaa ggaagaggaa gaggagaagg        360
aggaggaggg ggaggccaca aactcaacag tccccaggat cacgcctctg cctgacacct        420
acgggaccca gtaccatggc taaaccaggc ctgaacatgg agctgaatcg cctggtccag        480
gaccagccac ctggccagga gggccccaga cctggccccc caaacccagc cgagcacctc        540
cccaatgtgc ccagctaccg tcccgcaacc accgcatcc ccgtcctcgt ctcccggagg        600
acagccttgt ccaactccaa cttcaccaag gagatcagga gctccatccg tcgcctggta        660
ccagccacga agagcaccc ggagctccag gtggaagaca cagatgccga agctggcccc        720
ctcatcccag aggagacgat cccgccacct gagagaccac cagtgtctcc cgccaagtct        780
gacacccctcg cggttcccag cgcagcaacc cacaggaaga agctaccttc tcaggatgat        840
gaggctgaag aactcaaggc cctgtcaccg gctgagtccc cagtggttgc ctggtcagac        900
cccaccaccc cacaggaggc tgatggcgag gaccgtgcgg cctccacagc cagccagaac        960
agtgccatca tcaacgaccg gctccaggag ctggtgaaga tgttcaagga gcggacagag       1020
aaggtgaagg agaagctcat tgaccctgac gtcacctccg atgaggagag ccccaagccc       1080
tccccagcca gaaggcccc agactcagcc ccagcccaga agccggcgga ggcagaggcg       1140
gcagaggagg agcactactg tgacatgctc tgctgcaagt tcaagcgcag gccctggaag       1200
atgtaccagt tcccccagag catcgaccca ctgaccaacc tcatgtacat cctgtggctg       1260
ttcttcgtgg tgctggcctg gaactggaac tgctggctga ttcctgtgcg ctgggccttc       1320
ccgtaccagc gggcagacaa catccaactc tggctgctca tggactactt gtgcgacttc       1380
atctacctcc tggacatcac cgtgttccag atgcgtctcc agtttgtcaa aggcggggac       1440
atcattacag ataagaagga gatgcgtaat aattacctga agtctcaacg atttaagatg       1500
gacttgctct gccttttgcc tttggatttt ctctacttga aacttggcgt gaaccccctt       1560
cttcgcctgc cccgctgcct gaagtacatg gccttctttg agtttaataa ccgtctggaa       1620
gccatcctca gcaaagccta cgtttacagg gttatcagga ccaccgccta cctgctgtat       1680
agcttgcatc tcaactcctg tctttactac tgggcgtcgg ccttccaggg catcggttcc       1740
actcactggg tttatgacgg cgtggggaac agctacattc gatgctacta ctgggctgtg       1800
aaaactctca tcaccatcgg aggactgccc gaccccagag cgtcttttga gatcgtcttc       1860
cagctgctga attattttac aggtgtcttc gctttctctg tgatgattgg acagatgaga       1920
gatgtggtgg gggccgccac ggcagggcag acgtactacc gcagctgcat ggacagcacg       1980
gtgaagtaca tgaacttcta caagatcccc aggtctgtgc agaaccgcgt caagacctgg       2040

```
tatgagtaca cctggcattc acaaggcatg ctggatgagt cagagctgat ggttcagctt    2100
ccggacaaga tgcgtctgga cctggccatt gacgtaaact acaacattgt cagcaaagtg    2160
gcgctcttcc agggctgcga ccggcagatg atcttcgaca tgctcaagcg acttcgctca    2220
gtcgtctacc tacccaatga ctatgtgtgc aagaagggggg agattggccg agagatgtat    2280
attatccagg cggggcaggt gcaggtgctg ggcggcccag atggaaaggc tgtcctggtg    2340
acactcaaag ccggatcggt gtttggagag ataagcttgc tggctgtcgg gggcggtaac    2400
aggcgcacgg ccaatgtggt ggcccacggc ttcaccaatc tcttcattct ggataagaag    2460
gacttgaatg agattttggt gcattaccct gaatctcaga gctgctccg gaagaaggcc    2520 aggcgcatgc tcagaaacaa caacaaaccc aaggaggaga gagtgtgct catcctgccc    2580 ccacgtgcgg gcaccccgaa gctcttcaat gctgccctgg ctgcagcagg aaagatgggc    2640
cccaggggag ccaagggcgg caagctcgcc cacctgagag ccaggctcaa gaactggct    2700 gcactggagg cagccgcacg acagcagcag ctgctggaac aggccaagag ctcgcaagaa    2760 gccggggggag aggagggctc tggagccaca gaccaacctg caccccagga gccgtcagag    2820
cccaaggagc cccggagcc ccagccccg agttctccac cgccagcctc agcaaagccc    2880
gagggaagca cggaggaggc cgcagggccg ccggagcctt cagtgaggat ccgtgtgagt    2940
ccaggccctg atcccgggga acagacacta tcggtggaga tgctggaaga gaagaaggag    3000
gaggtggagt gaggtgcatt cagcaccctg atcccatccc taggtgcgga ccagacctt    3060 gaaccacctg cctcaccaag catcttagcc taaaggcgcc ttctcaccgg cttatagaaa    3120
ctctcaaatt tcatcaagta gtggtggtga cctcgagctc ctaacattcc cggagcaccc    3180
tgctcccctc tcacagttgc tattttctag aagaaaaccg ccttgcactt taaaaa      3236

<210> SEQ ID NO 3
<211> LENGTH: 2351
<212> TYPE: DNA
<213> ORGANISM: Rattus norvegicus

<400> SEQUENCE: 3
cgctggagcc cgagggcagc ctcttccagg aagccaggca ctttcccaag ccacctataa      60
tcggagaatc actggatagt ctacagacta gaaccacact acggaaacat gagccaggac     120
ggcaaagtga agaccacaga gtccacgccc ccagccccaa ccaaagccag gaagtggctg     180
ccagtcctag acccatctgg ggattactac tactggtggc tgaacacaat ggtcttccca     240
atcatgtaca acctcatcat cgttgtatgc agggcctgct ttcctgactt gcagcacagt     300
tacctggtgg cctggttcgt gctggactac acgagtgacc tgctgtacct actagatatt     360
ggggtacgct tccacacagg attcctagag cagggcatcc tggtggtaga caaaggcatg     420
atcgccagtc gctacgtccg cacctggagc ttcctgttgg acctggcgtc cctggtcccc     480
acagatgcgg cctatgtgca gctgggcccc cacatcccta cactccggct aaaccgcttt     540
ctccgagtgc ccgcctcctt cgaggctttt gatcgtacag agacccgcac ggcttaccca     600
aatgccttcc gcatagccaa gctgatgctt acatttttg ttgtcatcca ttggaacagt     660
tgcttatact tcgccctgtc caggtacctg gctttggac gggatgcgtg gtatacccca     720
gaccctgcgc aacctggctt tgagcgcttg cggcgccagt atctctacag cttctacttc     780
tccactctga tcctgaccac agtgggtgac acgccgctgc cagaccgaga ggaagagtac    840
ctcttcatgg tgggtgactt cctgctggcc gtcatggggt tcgccaccat catgggtagc    900
atgagctctg tcatttacaa catgaacact gcagatgcgg ccttctaccc agaccatgcg    960
```

-continued

```
ctggtaaaga agtacatgaa gctgcagcat gtcaacaaga ggctggagcg gcgagttatt    1020
gactggtacc agcatcttca gatcaacaag aagatgacca acgaggtagc catcttgcag    1080
cacctgcctg agcggctgcg ggcggaggtt gctgtgtccg tgcacctgtc taccctgagc    1140
cgagtacaga tcttccagaa ctgtgaagcc agcctgctgg aagagctggt gctgaagcta    1200
cagccccaga cctactcgcc aggcgaatat gtgtgccgca aggggacat tggccgagag     1260 atgtacatca tccgtgaggg ccagctggct gtggtggccg atgatggtgt cacacagtat    1320
gctgtgcttg gtgcagggct ctactttggg gagatcagta tcatcaacat caaagggaac    1380
atgtctggaa accgacgaac agccaacatc aagagcctag gttattcaga cctgttctgc    1440
ctcagcaagg aggatctgcg ggaggtactg agtgagtacc cacaggccca ggcggtcatg    1500
gaggagaagg gccgagaaat cttgctcaaa atgaataagt tggatgtgaa tgctgaggca    1560
gctgagatcg ccctccagga ggccacagag tctcggctca aaggcctcga ccagcagctt    1620
gatgatctgc agaccaagtt tgctcgccta ctggctgagc tggagtccag tgcactgaag    1680
atagcttacc gcatcgaaag gctggagtgg cagactcgag agtggccaat gccagaggac    1740
atgggtgagg ctgatgatga ggctgagcct ggagaaggga cgtccaagga tggagaggga    1800
aaggctggcc aggcgggacc ctcaggcata gaatgacccc gtcctgaccc taggactccc    1860
agctcaaata aatccagagt ggtgggaaag tctgcctgca ggaactgtca tcctctttgc    1920
taggttacag aacgtaggta aattggtcta tagatgccta gctagggatg tgggtcacag    1980
catccattag tcccatactc accagcaaat gtacacacac acacacacac aaacatgcgc    2040
acgcacacgc tcaagactga gttctacata atgttcctgt cttctgcaca catgtgcacc    2100
atgatcacag agaacaattg aatgcactgg gactcttgag gtaagcttta cacatcttaa    2160
aggaggtctg ctggtttagg gcaaggacag tgttggagct acagggaaag tagacagata    2220
caattcctga actctaggtc accacttcag ctgcttcagg gtatggcccg acttcaggtc    2280
tgagctggga caggcggtat tttgaaatga acctgatgtg tgatttatta ataaaatata    2340
aggttcataa c                                                         2351
```

<210> SEQ ID NO 4
<211> LENGTH: 1992
<212> TYPE: DNA
<213> ORGANISM: Artificial
<220> FEATURE:
<223> OTHER INFORMATION: Mutated CNG2

<400> SEQUENCE: 4

```
atgacagaaa aagccaatgg cgtgaagagc tccccagcca ataaccacaa ccaccatgcc      60
cctcctgcca tcaaggccag tggcaaagat gaccacaggg ccagcagccg gccacagtct    120
gctgctgctg atgacacctc ctcagagcta cagcaactgg cagagatgga tgccccccag    180
cagaggaggg gtggcttccg caggattgcc cgcctggtgg gggtcctcag agagtgggct    240
tacaggaact tccgtgagga ggagcctaga cctgactcat tccttgagcg tttccggggg    300
cctgagctcc acaccgtgac aacacaacaa ggagacggca aggcgacaa ggacggcgag     360 ggcaagggca ccaagaagaa gtttgaactc tttgtcttgg acccagccgg ggactggtac    420
taccgctggc ttttttctcat tgccttgccc gtcctctaca actggtgcct attggtggcc    480
agagcctgct tcagtgacct gcagaaaggc tactacatag tgtggctggt gctggattac    540
gtctcagatg tggtctacat cgcagacctc ttcatccgac tgcgcacagg tttcttggag    600
```

```
cagggctac tggtgaaaga caccaagaag ttgcgggaca actacatcca caccatgcag      660
tttaagctgg atgtggcctc catcatccct acagacctga tctattttgc tgtggggatc      720
cataaccctg aggtgcgctt caaccgcctg ctacactttg cccgcatgtt tgagttcttt      780
gaccgcactg agacacgcac cagctacccc aacatcttcc gaataagcaa cctgatcctc      840
tacatcttga tcatcattca ctggaatgcc tgcatctact atgccatctc caagtccatc      900
ggctttgggg tagacacctg ggtttacccc aacatcactg accctgagta tggctacctg      960
tctagggagt acatctattg cctttactgg tctacactga ccctcaccac cattggggag     1020
acaccacccc ctgtaaagga tgaggagtac ctgtttgtca tctttgactt cctgattggt     1080
gtcctcatct ttgccaccat cgtgggaaat gtgggctcca tgatctccaa catgaatgcc     1140 accgggctg agttccaggc caagattgat gctgtcaaac attatatgca gttccgaaag     1200
gtcagcaagg agatggaagc caaggtcatt aggtggtttg actacttgtg gaccaataag     1260
aagagtgtag atgagcgaga agtccctcaaa aacctgccag caaagctcag ggctgagata     1320
gccatcaacg tccacctgtc cacactcaag aaagtgcgca tctttcagga ctgtgaggct     1380
ggcctgctgt tggaactggt attaaagctc cggcctcagg tctttagccc tggggactac     1440
atttgccgca aggggatat tgggaaggag atgtacataa tcaaggaggg aaaattggca     1500
gtggtggctg atgacggtgt cactcagtat gccctgctct cggctgggag ttgctttgga     1560
gagatcagta tccttaatat taagggcagc aaaatgggca atcggcgcgc agccaacatc     1620
cgcagtcttg gctactctga tctgttctgc ttgtccaagg atgatcttat ggaagctgtg     1680
actgagtacc ctgatgccaa gagggtcttg gaggagagag gccgggagat tctgatgaag     1740
gagggcttgt tggatgagaa tgaggtggca gccagcatgg aggtagatgt gcaggaaaag     1800
ctagaacagc tggagaccaa catggacacc ttgtacactc gttttgcccg cctgctggcc     1860
gagtacacgg gagcccagca gaagctcaag cagcgcatca cagttttgga aacgaagatg     1920
aagcagaata atgaggatga ctccctgtca gatgggatga acagcccaga gccacctgcc     1980
gagaagccat aa                                                         1992

<210> SEQ ID NO 5
<211> LENGTH: 2641
<212> TYPE: DNA
<213> ORGANISM: Bos taurus

<400> SEQUENCE: 5
gtcgtcatgg cggaggatgc tgtgcgaggt ggatggcagc cttctcccca ggaccctcca       60
ggtccgagtc tgtggaggcc tcagcaactg gagtatgtgg acactgccat tcagcagcca      120
ccttggggtg gaatgtgaca cagcaagaag atggccaaga ttagcaccca atactcccac      180
cccaccagga cacacccctc ggtcaggacc atggacagag atctggattg cattgaaaac      240
ggtctcagca ggacccactt gccatgcgag gagacatcgt cagaactgca ggaaggcatt      300
gccatggaga ctagaggact ggctgaatcc aggcaaagct ccttcaccag ccagggtccc      360
accaggttgt cacgcctcat catctcgctc cgtgcctgga gcgccaggca cttacaccag      420
gaggaccaga ggcccgactc tttcctggag cgtttccgcg gagctgagct ccaagaggtg      480
tctagccgag aaagccatgt ccagttcaat gtgggcagcc aggagccacc agacagaggg      540
agaagtgcct ggcccctggc cagaaacaac accaacacct gcaacaactc ggagaaggat      600
gacaaggcga aaaaggagga gaaagagaaa aaggaagaga aaaaggagaa ccccaagaaa      660
gaggagaaga agaaggacag cgttgtgatg gacccttcca gcaacatgta ctaccactgg      720
```

```
ctgactgtca tcgccgtgcc tgtcttctac aactggtgtc tgctcgtgtg cagggcctgt      780
ttcgatgagc tccagtccga gcacctgatg ctttggctgg tcctggacta ctcagcagac      840
atcctctatg gcatggatat gctggtccga gcccggacag gcttcctgga gcaaggcctg      900
atggtcatgg acgccagccg gctgtggaag cactacacac agaccttgca cttcaagctg      960
gacgtgttgt ccctggtgcc cacagacctg gcttatttta agctgggcat gaactaccca     1020
gaactgaggt tcaaccgcct cctgaagttg gcccggctct tcgaattctt tgaccgcacg     1080
gagacaagga ccaactaccc caacatgttc aggatcggga acttggtctt gtacatcctc     1140
atcatcatcc actggaatgc ctgcatctac tttgccattt ccaagttcat tggtttcggg     1200
accgactcct gggtctaccc aaacgtctcc aacccagagt atgggcgcct ctccagaaag     1260
tacatttaca gtctctactg gtccaccttg accctgacca ccattgggga gaccccgccc     1320
cccgtaaaag acgaggaata tctctttgtg gtcatcgact tcctggtggg cgtcctgatt     1380
tttgccacca tcgtgggcaa cgtgggctcc atgatctcaa acatgaatgc ttcacgggcc     1440
gagttccagg ccaagatcga ttccatcaag cagtacatgc agttccgcaa ggtgaccaag     1500
gacttggaga cacgggtgat ccgctggttc gactacctgt gggccaataa gaagacagtg     1560
gatgagaagg aggtgctcaa gagcctcccc gacaagctga aggccgagat cgccatcaac     1620
gtgcacctgg acaccctgag gaaggtccga atcttccagg actgcgaggc ggggctgctg     1680
gtggagctgg tgctgaagct gcggccggca gtgttcagcc ccggggacta catctgcaag     1740
aagggggaca tcgggaggga gatgtacatt atcaaggagg gcaagctggc cgtggtggcc     1800
gaggacggca tcacccagtt cgtggtcctc ggcgacggga gttatttcgg ggagatcagc     1860
atcttgaaca tcaaggggag caagtccggg aaccgccgca cggccaacat caggagcatc     1920
ggctactcgg acctgttctg cctctccaag gacgacctga tggaggcgct caccgagtac     1980
cccgaggcca gaaggcgct ggaggagaaa gggcggcaga tcctcatgaa ggacaacctg     2040
atcgacgagg agctggccaa ggccggggca gaccccaagg acatcgagga aaggtggag      2100 cacctcgaga cctccctgga ctccctgcag accaggtttg cgcggctcct ggctgagtac     2160
aacgccaccc agatgaaggt gaagcagcgg ctcagccagt tggaaagcca ggtgaagatg     2220
ggcctcccgc ctgatggcga tgctccgcaa actgaggcca gtcagccctg aagacacagg     2280
tgccctctcc tgcctccccg gggcggcggt cagtgcgacg ctgcgccgca cggggctcgg     2340
ccgggaccga attctagctt tccccaccct ctgtgcgctg cgtggccttg ggagagagcc     2400
ttggtttccc tcatctagat aacaggactc tttatgtctg tcccagttaa gtgacaggtt     2460
gctgtgagct ccacaagaaa cgcttcgtga ggcagggttt tgttaagtgt gagatgtttc     2520
taggccaaga gtataaaaat gtgagcacag aagttgtttt ttttttttt ttttaatccg     2580 tgggaatat ttagactcct gaacttcatt tttttgtaa atgggaggtt atttacttac      2640
c                                                                    2641
```

TEST METHODS FOR DETERMINING THE INTRACELLULAR CONCENTRATION OF CYCLIC NUCLEOTIDES

CROSS REFERENCE TO RELATED APPLICATIONS

This application is National Stage Entry of PCT/EP04/02317 filed Mar. 6, 2004, which claims the benefit of DE 103 11 769.5, filed Mar. 18, 2003.

BACKGROUND OF THE INVENTION

The invention relates to processes for the quantiative optical analysis of the intracellular concentration of cyclic guanosine 3',5'-monophosphate (CGMP) or cyclic adenosine 3',5'-monophosphate (cAMP). These processes may be useful for identifying and evaluating the pharmacological properties of test substances which influence the activity of receptors or enzymes involved in the synthesis or degradation of the cyclic nucleotides cGMP and cAMP. As a result, the process is suitable, for example, for finding modulators of soluble and membrane-bound guanylate cyclases, phosphodiesterases (PDEs), NO synthases and G-protein-coupled receptors (GPCRs).

The invention describes a process in which the intracellular concentrations of cGMP or cAMP are measured with the aid of recombinant cell lines. These cell lines express recombinantly a combination of particular ion channels activated by cyclic nucleotides (CNG channels), a calcium-sensitive photoprotein and a receptor or an enzyme for which modulators are to be found. The process is suitable for automation and for high-throughput screening (HTS) and ultra high-throughput screening (uHTS) for modulators.

Current processes for measuring the intracellular concentration of cGMP or cAMP have the disadvantage of being very expensive, due to the use of radioactivity, being only partially automatable, if at all, and being very complicated.

Conventional commercial systems for determining cGMP and cAMP are radioactive techniques such as the radioimmunoassay (RIA; e.g. from IBL, Hamburg, Germany), the scintillation proximity assay (SPA; Amersham Bioscience, UK) and the non-radioactive enzymed-linked immunosorbent assay (ELISA; for example from Amersham Bioscience, UK).

The above-described processes cannot be used for measuring the intracellular cGMP and cAMP concentrations in living cells "in situ". To carry out the measurements, the cells need to be disrupted and the cyclic nucleotides then be extracted.

Another process for measuring intracellular cAMP is the measurement with the aid of inducible promoter systems ("cAMP response element", CRE) and the enzyme luciferase (Goetz et al., J. Biomol. Screen. (2000) 5 377-384). The process has the disadvantage, however, that both transcription and translation need to take place in order for the signal to form, causing the measurement to last for hours. This method is thus not suitable for rapid measurement of the actual cAMP concentrations in cells.

BRIEF SUMMARY OF THE INVENTION

It is the object of the invention to find an improved, non-radioactive process for measuring the intracellular concentrations of cGMP and cAMP. The intention here is to be able to carry out the measurements very rapidly and also with high sensitivity. The process should be automatable and suitable for high-throughput screening of samples or test compounds (HTS and uHTS).

Test compounds in accordance with the invention are preferably small-molecule chemical compounds having a molecular weight of from 100 to 500 or 100 to 1000 or else higher than that. These compounds may be used individually or else as a mixture in the processes according to the invention. Test compounds in accordance with the invention also include antibodies, natural substances, extracts of natural substances, peptides, proteins and nucleic acids. This list is to be regarded only by way of example and not as finite.

DETAILED DESCRIPTION OF THE INVENTION

Figure 1:
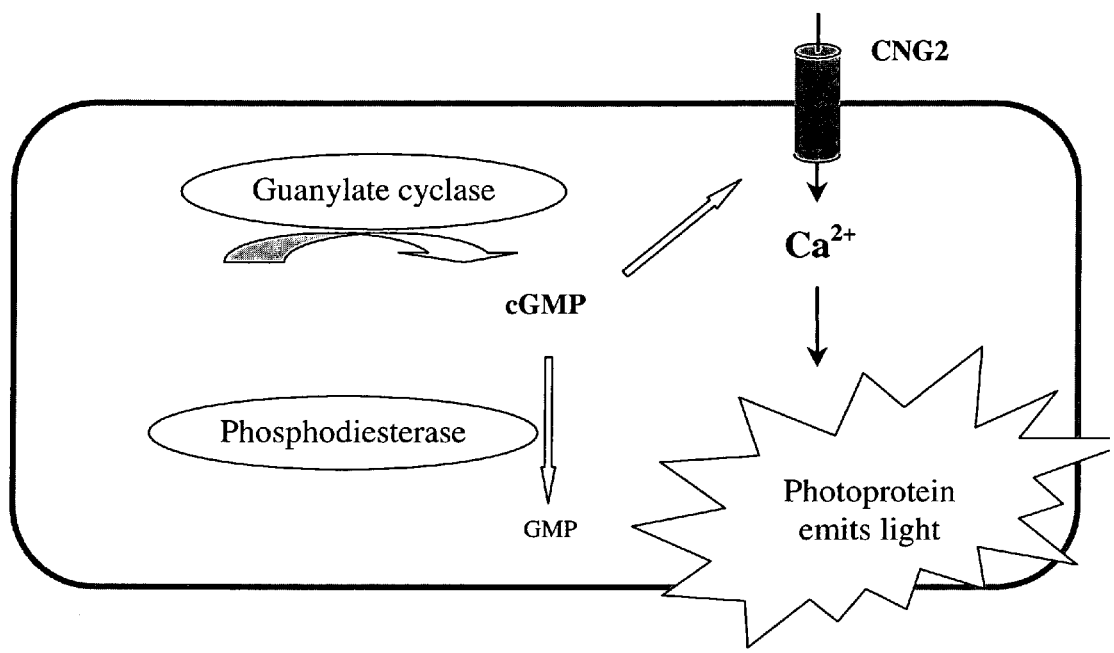
FIG. 1: Schematic representation of the process for determining intracellular cGMP concentration.

In order to establish a screening system for enzymes and receptors which influence the intracellular cAMP or cGMP level, various ion channels activated by cyclic nucleotides (CNG channels) are transfected, alone or in various combinations, into cells which additionally express a calcium-sensitive photoprotein in a recombinant manner. These cells are subsequently transfected with various enzymes or receptors in order to test the suitability of the cells for high-throughput screening. This involves using, for example, soluble guanylate cyclase, since it is capable of producing intracellular cGMP after stimulation. An example of a receptor which may be used is the β-adrenergic receptor which, after an activation, induces an increase in intracellular cAMP concentration.

CNG channels are integral membrane proteins which are opened by the cyclic nucleotides cGMP and cAMP. This family of ion channels are non-selective cation channels which are permeable to sodium, potassium and calcium ions. The functional channels are composed of four identical or else different subunits (homo- or heterotetramers). The sensitivities to cGMP and cAMP can be influenced by combining various subunits (Biel et al. TCM (1996) 6, 274-280; Kaupp and Seifert, Physiol. Rev. (2002) 82, 769-824). The channel subunits CNG1-CNG6 which, according to a more recent nomenclature, are also referred to as CNGA1-CNB3, have been cloned and published (Bradley et al., Science (2001)

294, 2095-2096). There exist also splice variants such as CNG4.3, for example (Sauter et al., PNAS (1998) 95, 4696-4701).

The increase in intracellular cGMP or cAMP concentration results in the opening of the CNG channels and thereby in an influx of calcium ions. The calcium flowing in may then be detected with the aid of calcium-sensitive fluorescent indicators, such as, for example, FURA, Fluo-3 etc., or with the aid of calcium-sensitive photoproteins such as aequorin or obelin.

The photoprotein aequorin which is derived from the jellyfish *Aequorea victoria* is a highly sensitive calcium indicator in cells. The aequorin complex consists of the protein apoaequorin, molecular oxygen and the luminophore coelenterazine. This complex emits blue light in the presence of calcium ($Ca^{2+}$ ions), with maximum emission at 466 nm (Jones et al., Trends Biotechnol. (1999) 17, 477-481).

Another photoprotein is obelin which has been cloned from various hydrozoa such as *Obelia longissima*, for example. It consists of apoobelin, $O_2$ and the luminophore coelenterazine. Likewise, blue light is emitted in the presence of calcium (Illarionov et al., Methods Enzymol. (2000) 305, 223-49).

Guanylate cyclases are responsible for producing cGMP from GTP. A distinction is made between soluble and membrane-bound guanylate cyclases. Soluble guanylate cyclase is a heterodimer composed of an alpha1 subunit and a beta1 subunit. It is the natural receptor for nitrogen monoxide (NO) produced by the endothelial NO synthase and can therefore also be activated pharmacologically by NO-releasing substances such as, for example, SIN-1. Since the cGMP produced by guanylate cyclase induces relaxation of blood vessels, the enzyme is a highly interesting pharmacological target (Hobbs A J., TIPS (1997) 18, 484-491). The membrane-bound guanylate cyclases possess a transmembrane segment and are activated by various agonists such as ANP, BNP, CNP or guanylin (Wedel and Garbers, Annual Rev. Physiol. (2001) 63, 215-233).

Another pharmacologically interesting protein family are the "G-protein-coupled receptors" (GPCRs). These are integral membrane proteins which can transduce the action of an extracellular hormone into the cell interior. The intracellular levels of cAMP or calcium are influenced via coupling of these receptors to various G proteins. The activation of "Gq-coupled receptors" results in a release of calcium from internal stores and thus in an increase in cytoplasmic calcium concentration. The activation of "Gs-coupled receptors" results in an increase in cAMP concentration, whereas activation of the "Gi-coupled receptors" reduces the intracellular cAMP content (Gurrath M., Curr. Med. Chem. (2001) 8, 1605-1548). An example of Gs-coupled receptors are the "β-adrenergic receptors" which can be stimulated with the aid of agonists such as isoprenaline (Dzimiri N., Pharmakol. Rev. (1999) 51, 465-501).

The cyclic nucleotides cGMP and cAMP produced by guanylate cyclases and GPCRs, respectively, are hydrolyzed by "phosphodiesterases" (PDEs) to give GMP and AMP, respectively. The phosphodiesterases are an enzyme family whose members are distinctly different with regard to substrate specificity, regulation and expression patterns in the body (Francis et al., Prog. Nucleic Acid Res. Mol. Biol. (2001) 65, 1-52). PDEs play a decisive part in controlling the intracellular cAMP and cGMP levels and are therefore likewise important targets for pharmacological intervention.

Surprisingly, combining the CNG3 channel (SEQ ID NO: 5, Acc. No. X 89600) or, in particular, the CNG2 channel (SEQ ID NO: 1, Acc. No. X55010) with a photoprotein proved to be particularly suitable for detecting changes in intracellular cGMP concentrations (FIG. 1).

Figure 3:
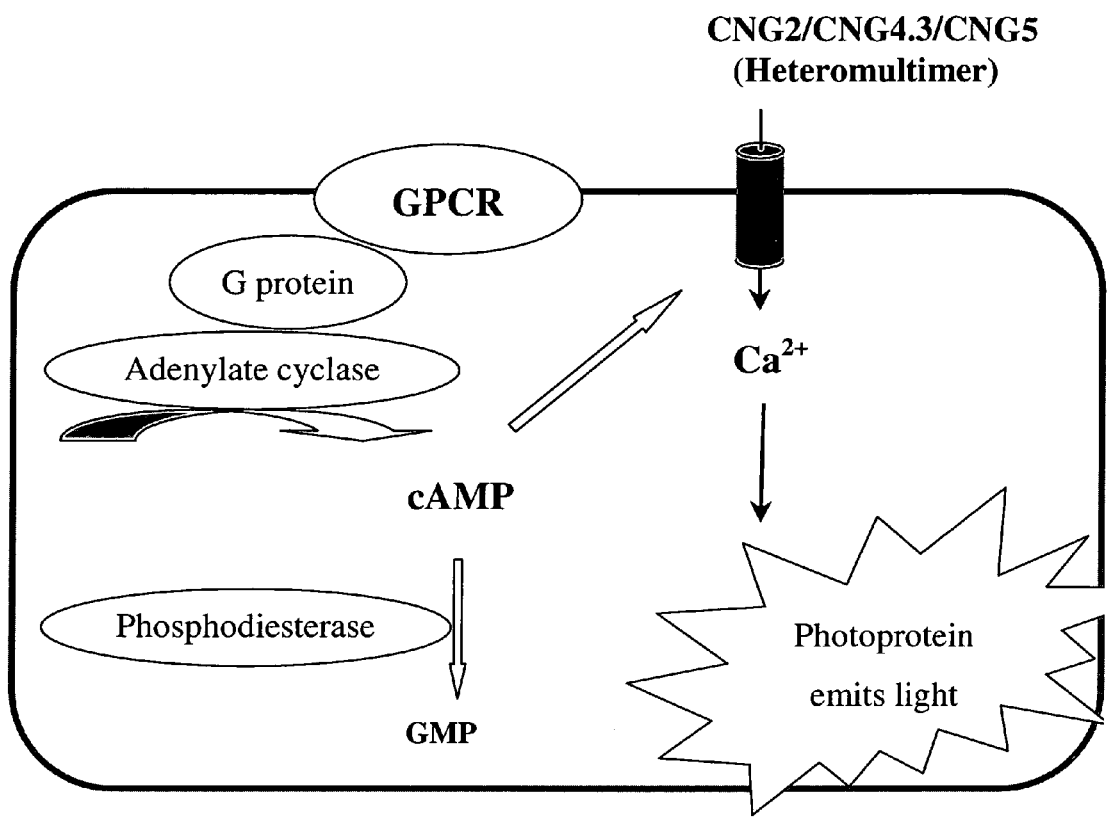
FIG. 3: Schematic representation of the process for determining intracellular cAMP concentration.

A similar surprise was a combination of CNG2/CNG4.3/CNG5 (SEQ ID NO: 1/SEQ ID NO: 2, Acc. No. AJ000515/SEQ ID NO: 3, Acc. No. U12623) and a photoprotein, which proved to be very suitable for detecting changes in intracellular cAMP concentration (FIG. 3). The combination of CNG2(T537A)/CNG4.3/CNG5 (SEQ ID NO: 4/SEQ ID NO: 2/SEQ ID NO: 3) with a photoprotein proved to be particularly suitable for cAMP measurement. In the CNG2 mutant CNG2(T537A) (SEQ ID NO: 4), the amino acid threonine-537 has been replaced with alanine (Altenhofen et al., PNAS (1991) 88, 9868-9872).

The recombinant cell lines may be prepared using common vectors such as pcDNA1.1 Amp or pcDNA3 (Invitrogen Life Technologies). Common transfection reagents such as, for example, lipofectamine (Invitrogen Life Technologies) may be used for transfecting the corresponding plasmid constructs.

The cells are seeded for the measurements on 384-well microtitre plates (MTPs) at 1500 cells per well and on 1536-well MTPs at 250 cells per well. After 1-2 days of growth at 37° C./5% $CO_2$, the cell culture medium (DMEM/F12 containing 10% foetal calf serum) is removed and the cells are charged with coelenterazine (0.8 µg/ml) in calcium-free Tyrode's at 37° C./5% $CO_2$ for 3 h. Subsequently, test substances and appropriate control substances (e.g. SIN-1 or isoprenaline) are added in calcium-free Tyrode's and incubated on the cells for 5-10 min. The extra measurement is then carried out in a light-tight box by adding calcium-containing Tyrode's via a comb (final calcium concentration: 3 mM), with the aid of a charge-coupled device camera.

Figure 5:
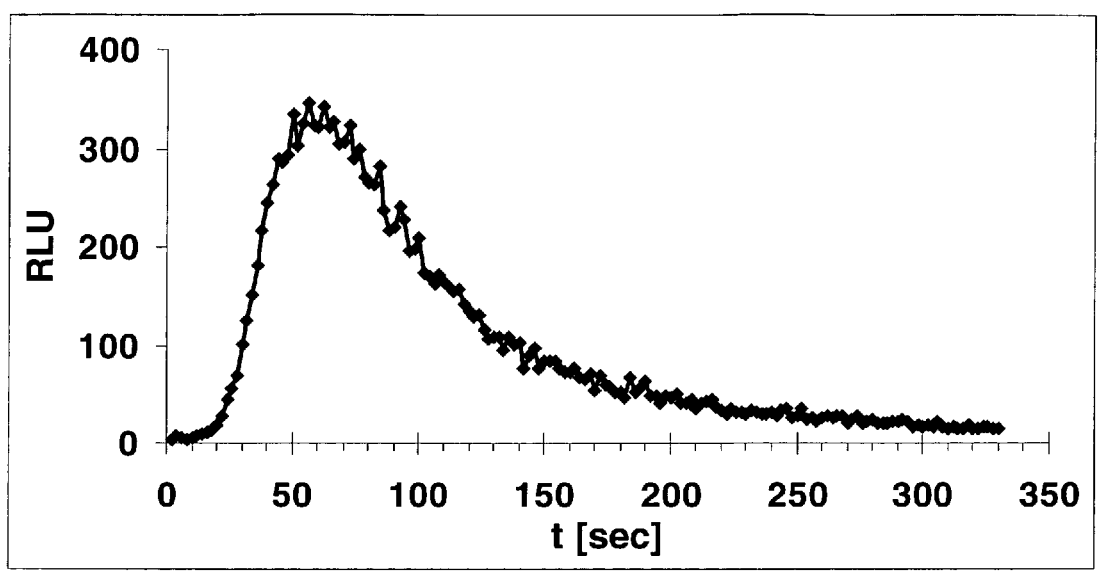
FIG. 5: Kinetics of the luminescence signal after activation of the B-adrenergic receptor with isoprenaline in calcium-containing Tyrode's. The measurement is started with the addition of the agonist isoprenaline ($10^{-6}$ M) within the light-tight box.

To measure the effects of substances directly, the cells are charged with coelenterazine in calcium-containing Tyrode's. The substances are then added within the light-tight box and measurement commences immediately with addition of the substances (FIG. 5).

The advantages of this process are the high sensitivity of the measurement, the low costs per measuring point and the suitability for HTS and uHTS. The process has an excellent signal-to-noise ratio, and it is possible to achieve stimulation factors of 50-150. It is moreover possible to apply test substances for very short periods of time, since a signal can already be observed after a few seconds (FIG. 5). This has the advantage of unspecific effects of test substances (e.g. due to cytotoxicity) on the cells used being minimized. The process is moreover suitable for characterizing "orphan receptors" (receptors whose natural ligand is unknown), since it is possible to observe both changes in the cAMP level (Gs coupling and Gi coupling) and changes in intracellular calcium concentration (Gq coupling) by means of luminescence or fluorescence measurement.

The invention relates to processes for determining the intracellular concentration of cyclic nucleotides, characterized in that a cell expressing a CNG channel together with a photoprotein is prepared and used, and the intracellular concentration of cyclic nucleotides is determined by means of the luminescence signal of the photoprotein.

The invention likewise relates to processes as described above, wherein the CNG channel is the CNG2 or the CNG3 channel.

The invention comprises processes as described above, wherein the cyclic nucleotide is cGMP.

The invention likewise relates to processes as described above, wherein the cyclic nucleotide is cAMP and a cell expressing a combination of the CNG2/CNG4.3/CNG5 channels is prepared and used.

The invention also relates to the above-described processes, wherein the cyclic nucleotide is cAMP and a cell expressing a combination of the CNG2(T537A)/CNG4.3/CNG5 channels is prepared and used.

The invention relates to the processes as described above, wherein the photoprotein is aequorin.

The invention also relates to processes as described above, wherein the photoprotein is obelin.

The invention relates to a method of screening test compounds for identifying receptor ligands, wherein any of the above-described processes is used in which the cell used expresses the receptor and possesses an intracellular messenger system which allows a receptor-ligand bond to cause measurable modulation of the ion flow through the ion channel, the said cell is incubated with test substances of which those modulating the luminescence are selected.

The invention also relates to a method of this type, wherein the receptor is a G-protein-coupled receptor.

The invention also relates to a corresponding method, wherein the G-protein-coupled receptor is an orphan receptor.

The invention furthermore relates to a method of screening test compounds for identifying modulators of phosphodiesterases, wherein any of the above-described processes is used in which the cell used expresses the phosphodiesterase, the said cell is incubated with test substances of which those modulating the luminescence are selected.

The invention likewise relates to a method of screening test compounds for identifying modulators of guanylate cyclases, wherein any of the above-described processes is used in which the cell used expresses the guanylate cyclase, the said cell is incubated with test substances of which those modulating the luminescence are selected.

The invention also comprises a method of screening test compounds for identifying modulators of NO synthase, wherein any of the above-described processes is used in which the cell used expresses the NO synthase and soluble guanylate cyclase, the said cell is incubated with test substances of which those modulating the luminescence are selected.

The invention also relates to a corresponding method, wherein the NO synthase and the soluble guanylate cyclase are expressed in different cells.

The invention also relates to a cell prepared by any of the processes illustrated above.

EXAMPLES

Figure 2:
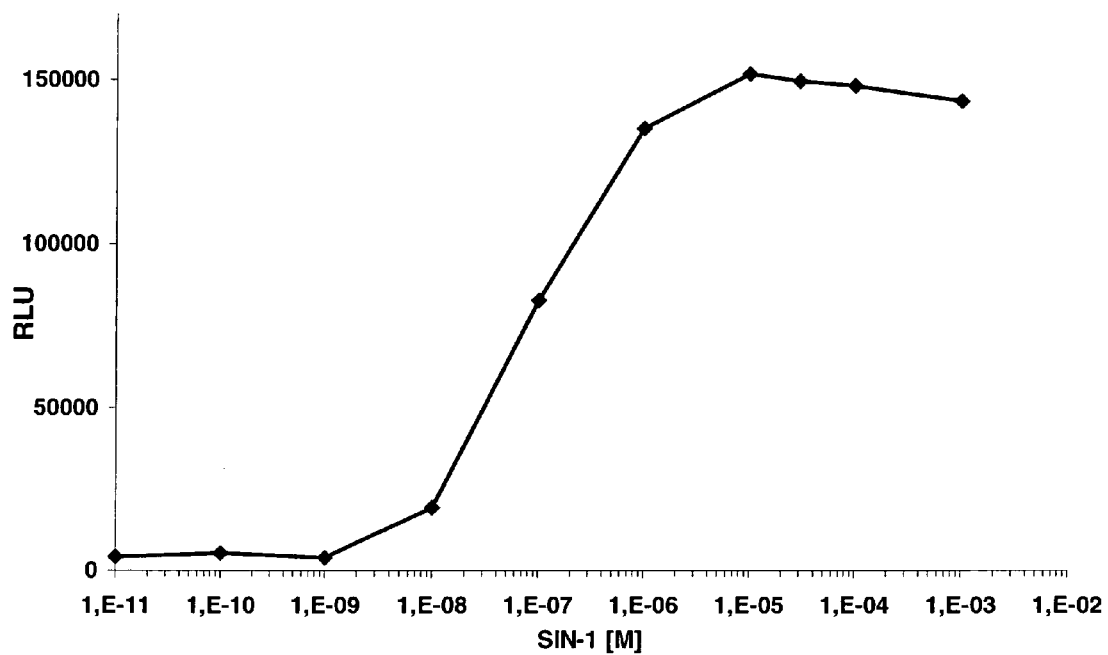
FIG. 2: Luminescence measurement after activation of soluble guanylate cyclase with SIN-1. The "relative light units" (RLUs) were measured for 1 min. The amount of light measured at the SIN-1 concentration indicated over this period is shown.

If, for example, soluble guanylate cyclase is additionally expressed in a cell line which expresses, as a cGMP measuring system, the CNG2 channel (SEQ ID NO: 1) together with a calcium-sensitive photoprotein, it is possible to increase the intercellular cGMP concentration with the aid of the guanylate cyclase stimulator SIN-1 in a dose-dependent manner and to detect an enhanced luminescence signal (FIG. 2).

Figure 4:
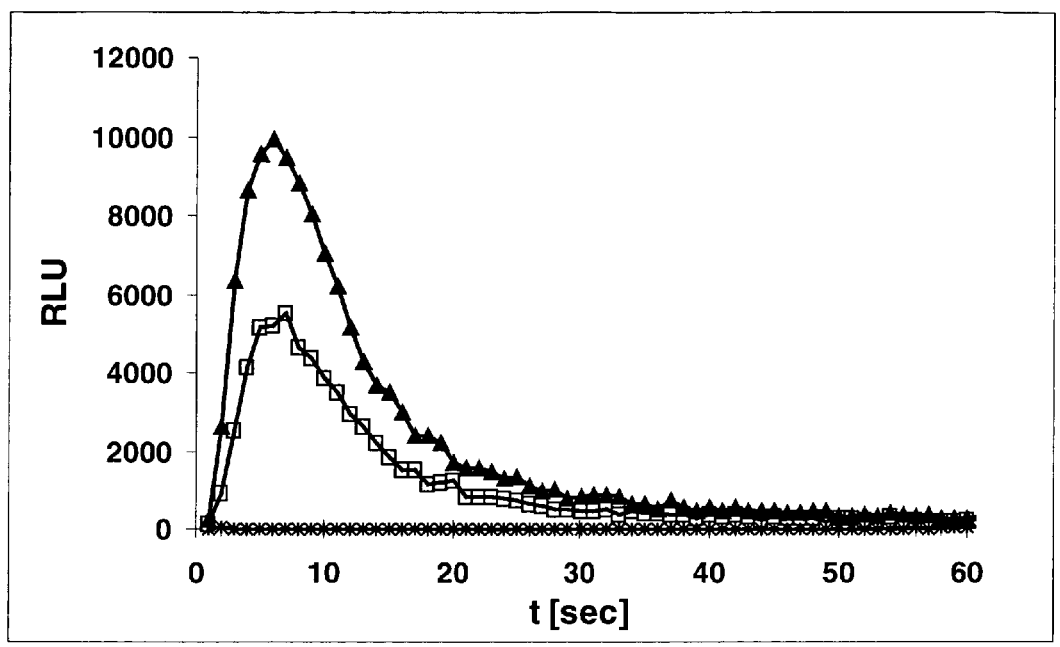
FIG. 4: Luminescence measurement after activation of the .beta.-adrenergic receptor with isoprenaline. The incubation time with isoprenaline is 10 min in calcium-free Tyrode's. Measurement is started by adding calcium. The relative light units (RLUs) are measured in second intervals. The time course of the luminescence signal after addition of calcium and previous incubation with 0 M (stars), $10^{-7}$ M (squares) and $10^{-6}$ M (triangles) isoprenaline is shown.

If, for example, the β-adrenergic receptor is additionally expressed in cells which, as a cAMP-measuring system, express a calcium-sensitive photoprotein together with the CNG-channel subunits CNG2(T537A)/CNG4.3/CNG5 (SEQ ID NO: 4/SEQ ID NO: 2/SEQ ID NO: 3), activation of this receptor by means of isoprenaline results in a dose-dependent manner in an increased cAMP concentration and an enhanced lumiscence signal (FIG. 4). If the cells are charged with coelenterazine in calcium-containing Tyrode's, the agonist isoprenaline may also be added directly to the cells within the light-tight box. A lumiscence signal will then be observed within a few seconds (FIG. 5).

The invention claimed is:

1. Process for determining the intracellular concentration of cyclic nucleotides, comprising i) a cell expressing a CNG channel together with a photoprotein, ii) allowing said photoprotein to produce a luminescence signal;

and iii) determining the intracellular concentration of cyclic nucleotides by means of the luminescence signal of the photoprotein.

2. The process according to claim 1, wherein the CNG channel is the CNG2 or the CNG3 channel.

3. The process according to claim 1 or 2, wherein the cyclic nucleotide is cGMP.

4. The process according to claim 1, wherein the cyclic nucleotide is cAMP and the cell expresses a combination of the CNG2/CNG4.3/CNG5 channels.

5. The process according to claim 4, wherein the cyclic nucleotide is cAMP and the cell expresses a combination of the CNG2(T537A)/CNG4.3/CNG5 channels.

6. The process according to claim 1, wherein the photoprotein is aequorin.

7. The process according to claim 1, wherein the photoprotein is obelin.

8. A method of screening test compounds in order to identify a ligand for a cell surface receptor which modulates the intracellular concentration of cyclic nucleotides comprising;
(i) contacting a cell expressing a CNG channel together with a photoprotein with a test compound; and
(ii) determining the level of intracellular concentration of cyclic nucleotides in said cell according to the process of claim 1
wherein a modulation of the level of intracellular concentration of cyclic nucleotides caused by said test compound indicates said test compound is a ligand for said receptor.

9. The method according to claim 8, wherein the receptor is a G-protein-coupled receptor.

10. The method according to claim 9, wherein the G-protein-coupled receptor is an orphan receptor.

11. A method of screening test compounds for identifying modulators of phosphodiesterases using a process according to claim 1 wherein the cell used expresses a phosphodiesterase and the cell is incubated with test substances which are selected by the modulating of the luminescence produced.

12. A method of screening test compounds for identifying modulators of guanylate cyclase using a process according to claim 1 wherein the cell used expresses guanylate cyclase and, the cell is incubated with test substances of which are selected by the modulating of the luminescence produced.

13. A method of screening test compounds for identifying modulators of NO synthase using a process according to claim 1 wherein the cell used expresses NO synthase and soluble guanylate cyclase and the cell is incubated with test substances which are selected by the modulating of the luminescence produced.

14. A method according to claim 13, wherein the NO synthase and the soluble guanylate cyclase are expressed in different cells.

15. An isolated cell which expresses a CNG channel and a photoprotein.

16. The isolated cell of claim 15, wherein the CNG channel is the CNG2 or the CNG3 channel.

17. The isolated cell of claim 15, wherein the cell expresses a combination of the CNG2/CNG4.3/CNG5 channels.

18. The isolated cell of claim 15, wherein the cell expresses a combination of the CNG2(T537A)/CNG4.3/CNG5 channels.

19. The isolated cell of claim 15 wherein said photoprotein is aequorin.

20. The isolated cell of claim 15 wherein said photoprotein is obelin.

* * * * *